(12) United States Patent
Stoddart et al.

(10) Patent No.: US 7,221,969 B2
(45) Date of Patent: May 22, 2007

(54) METHOD AND APPARATUS FOR DETERMINING CEREBRAL OXYGEN SATURATION

(75) Inventors: Hugh F. Stoddart, Groton, MA (US); Hugh A. Stoddart, Harvard, MA (US); Thomas Christopher John Sefranek, Shirley, MA (US); Timothy Olden, Nashua, NH (US); Dale Martin, Lunenburg, MA (US)

(73) Assignee: Neurophysics Corporation, Shirley, MA (US)

( * ) Notice: Subject to any disclaimer, the term of this patent is extended or adjusted under 35 U.S.C. 154(b) by 143 days.

(21) Appl. No.: 10/506,158

(22) PCT Filed: Feb. 27, 2003

(86) PCT No.: PCT/US03/05868

§ 371 (c)(1),
(2), (4) Date: Jan. 18, 2005

(87) PCT Pub. No.: WO03/071928

PCT Pub. Date: Sep. 4, 2003

(65) Prior Publication Data

US 2005/0119542 A1    Jun. 2, 2005

Related U.S. Application Data

(60) Provisional application No. 60/359,829, filed on Feb. 27, 2002.

(51) Int. Cl.
*A61B 5/00* (2006.01)

(52) U.S. Cl. .................................. 600/323; 600/310
(58) Field of Classification Search ................ 600/322, 600/323, 324, 310, 326, 328, 338
See application file for complete search history.

(56) References Cited

U.S. PATENT DOCUMENTS

| 5,524,617 | A | 6/1996 | Mannheimer |
| 5,770,454 | A | 6/1998 | Essenpreis et al. |
| 6,241,663 | B1 | 6/2001 | Wu et al. |
| 6,381,480 | B1 * | 4/2002 | Stoddart et al. ............ 600/338 |

FOREIGN PATENT DOCUMENTS

WO    WO 99/26528    *  3/1999

* cited by examiner

*Primary Examiner*—Eric Winakur
*Assistant Examiner*—Etsub Berhanu
(74) *Attorney, Agent, or Firm*—Price, Heneveld, Cooper, DeWitt & Litton, LLP

(57) ABSTRACT

A new and improved method and apparatus for determining cerebral oxygenation. In one basic aspect, a new processing methodology for oxygenation determination, in particular cerebral oxygenation, is provided based on the apprehension and discovery that time-based photon quantity determinations of the wavelength-specific light leaving the head of the patient may be significantly improved, and simplified, by determining the quantity of returning photons in at least one set of two different but closely spaced points in time following the instant of injection, and then taking the ratio of the determinations in each set, to thereby cancel and remove several important sources of error.

24 Claims, 4 Drawing Sheets

METHOD AND APPARATUS FOR DETERMINING CEREBRAL OXYGEN SATURATION

CROSS-REFERENCE TO RELATED APPLICATION

The present invention is related to that disclosed and claimed in prior International Application No. PCT/US98/25236 filed PCT on 25 Nov. 1998, and U.S. patent application Ser. No. 09/555,351 based thereupon, filed on May 26, 2000, entitled METHOD AND APPARATUS FOR MONITORING FETAL CEREBRAL OXYGENATION DURING CHILDBIRTH (now U.S. Pat. No. 6,381,480), and also to U.S. provisional Application No. 60/359,829 filed Feb. 27, 2002, entitled METHOD AND APPARATUS FOR DETERMINING CEREBRAL OXYGEN SATURATION, on which priority is hereby claimed. All such prior applications are incorporated herein by reference as completely as though set forth verbatim.

BACKGROUND OF THE INVENTION

In the first above-identified previously filed patent application, a new concept is disclosed for determining the state of hemoglobin oxygen saturation in brain tissue, particularly fetal brain tissue, that is especially useful during the critical time of childbirth. Basically, this approach utilizes the concept of injecting a very short pulse of light at a selected wavelength in the near-infrared range (e.g. one nanosecond (ns) in length) into the head via a fiberoptic cable optically coupled to the head, detecting the corresponding photons emerging from the head into an adjacent detector and fiberoptic cable after a first very short period (e.g., one ns) and then detecting emerging photons once again after at least one more very brief period (on the order of 4 to 5 ns).

The injected pulse of photons (sometimes referred to as a "bolus") spreads out from the injection site in the form of a rapidly expanding "glowball," due to the extensive amount of scatter which occurs in this medium (on average, photon direction becoming completely randomized after only 0.6 mm of travel), and this translates into photon pathlength. Therefore, the detection of differing amounts of photons leaving the head at different relatively short intervals corresponding to photon travel over different effective pathlengths within the brain, which represents, and characterizes, differing depths of photon travel within the brain tissue. Thus, the quantities of photons detected at different intervals in effect sample different depths of travel, and hence different volumes of brain tissue. As a result, mathematical processing and correlation of these differential results will be directly indicative of differing amounts of photon absorption at different depths, including the amount of photon reduction which results (for example) from absorption by hemoglobin molecules. By using selected wavelengths of injected light, the amount of hemoglobin oxygenation can thus be determined, due to the difference in oxygen absorption as opposed to reduced or non-oxygenated hemoglobin, on a wavelength-specific basis.

The aforementioned U.S. Pat. No. 6,381,480 discloses this technological concept in considerably greater detail, together with representative and then-contemplated preferred embodiments of apparatus and methodology for implementing the concept to create a useful fetal cerebral oximeter. As may be seen by further study of that patent, it will be seen that the disclosed apparatus basically includes a source of photons coupled to the head by a fiberoptic conductor which leads to an injection site (e.g., the forehead), plus a fiberoptic leading from a photon detection device that basically comprises at least two shuttered detectors which are gated open for a very brief period (on the order of ins) at specific time intervals after the instant of injection, preferably by using a trigger signal obtained from a fiberoptic conductor that transmits a small fraction of the photons emitted by the source to the shuttered detectors at different and specifically timed intervals.

SUMMARY OF THE INVENTION

The present invention comprises a new and improved method and apparatus for determining cerebral oxygenation based on the underlying concept of the aforementioned earlier patent, obtained by way of a novel implementation of such concept, and this forms the basis of the present patent, in which a disclosure is provided for a preferred embodiment of such implementation.

In one basic aspect, the present invention recognizes and provides a new processing methodology for oxygenation determination, in particular cerebral oxygenation as briefly noted above, based on the apprehension and discovery that time-based photon quantity determinations of the wavelength-specific light leaving the head of the patient may be significantly improved, and simplified, by determining the quantity of returning photons in at least one set of two different but closely spaced points in time following the instant of injection, and then taking the ratio of the determinations in each set, to thereby cancel and remove several important sources of error.

Furthermore, and in a more particular sense, the invention provides a novel and advantageous implementation of the methodology just described, by which the detection equipment is simplified and certain components shown in the implementation of U.S. Pat. No. 6,381,480 eliminated, thereby providing substantial economies of manufacture, with related reduction of costs to users of the technology.

DESCRIPTION OF THE PREFERRED EMBODIMENTS

Figure 1:
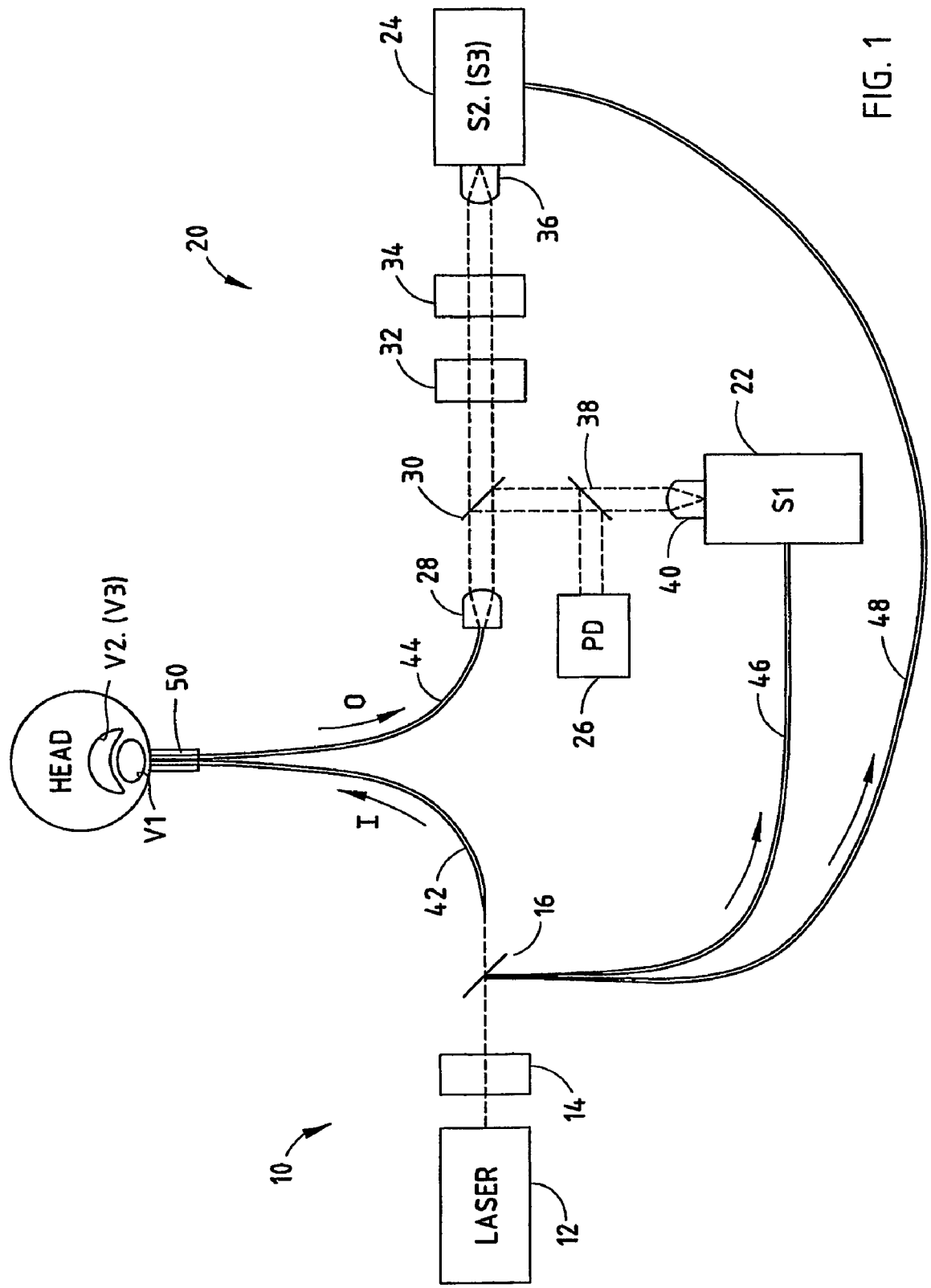
FIG. 1 is a block diagram of the basic system and equipment disclosed in the aforementioned prior and related patent, corresponding to FIG. 3 thereof.

Inasmuch as an understanding of the present invention requires an understanding of the invention disclosed in the aforementioned prior related patent of the present inventors, FIG. 1 herein depicts the overall system of a preferred embodiment then contemplated, and an abbreviated commentary with respect thereto follows.

A very short (on the order of ins) pulse of photons at a selected wavelength in the near infrared range is provided by a source 10 and is conducted to the head ("HEAD") of the patient (fetus) by a fiberoptic cable 42 (photon travel designated "I" and shown with an arrow), and resulting photons exiting the head at brief intervals after that are detected at a point closely adjacent the point of entry at two (or more)

closely spaced points in time (for example, on the order of 4 ns and 5 ns after injection). These detected photons are then coupled to a photon detection apparatus 20 that includes at least first and second shuttered detectors 22 and 24, via a receiving fiberoptic cable 44 (labeled "O"), after passing through a lens 28, partially reflecting mirrors 30 and 38, an auxiliary shutter 32, and a fluorescence-blocking filter 34. The total flow of photons exiting the head via cable 44 is monitored by a photodiode detector 26, to which a small fraction of such light is directed by partially reflecting mirror 38. Shuttered detectors 22 and 24 are gated open by a small amount of the light from source 12, via fiberoptic cables 46 and 48, which are accurately cut to precise lengths that will provide the desired time delay for sampling the exiting photon stream after the instant of injection.

Accordingly, the shuttered detectors 22 and 24 provide outputs which represent the amount of photons exiting the head at the corresponding points in time, and by choosing wavelengths which are selectively absorbed by oxygenated and reduced hemoglobin, a precise and accurate determination of cerebral oxygenation may be obtained. In this regard, the longer the time delay from the instant of insertion, the deeper the photons will travel within the brain due to the effects of scatter, as noted above. Therefore, the longer this duration (and deeper the extent of travel), the more absorption these photons will incur before they exit the brain and skull, etc. For these reasons, it may be advantageous to implement more than one of the longer periods of delay, and also to utilize an alternating wavelength set, since this enables the determination of oxygenation with attendant suppression of subject-dependent parameters and variations in skin contact.

Figure 2:
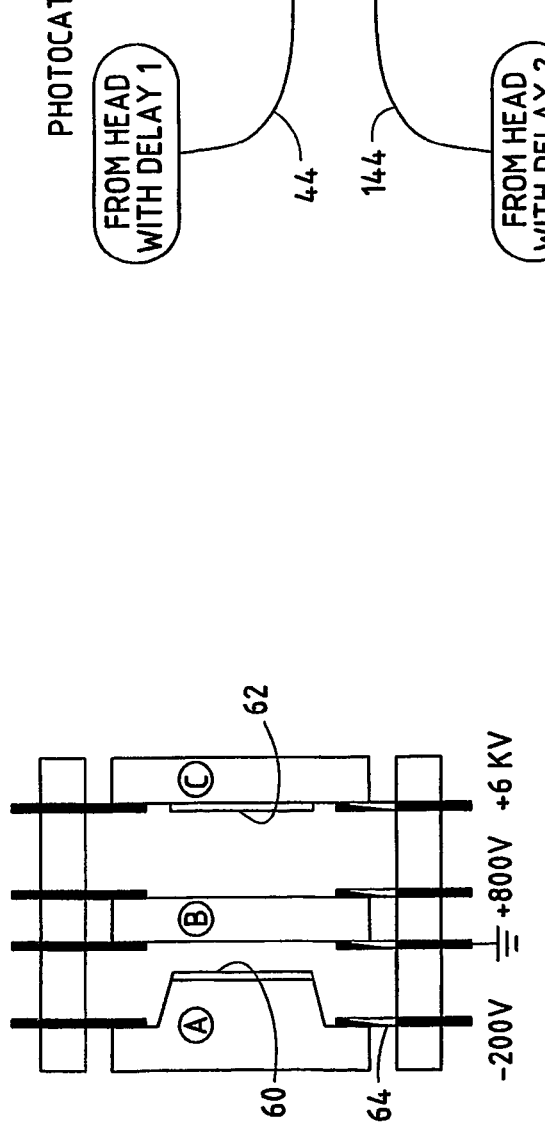
FIG. 2 is an enlarged representation of an image intensifier as shown in the aforementioned prior and related patent, corresponding to FIG. 4 thereof.

The aforementioned shuttered detectors 22 and 24 must be very fast-acting, going from completely off to completely on in about ins, or less. Errors in turn-on relative to the instant of pulse injection cannot be tolerated even if amounting only to a few nanoseconds (i.e., one or more). A satisfactory shutter and detector can be implemented by using a fast, linear, focused-dynode PMT; however, in a preferred first embodiment, an image-intensifier of the type widely used in night-vision devices was utilized with good results, and a schematic cross section of a typical proximity-focused such image intensifier, as utilized in the earlier patent, is illustrated in FIG. 2. Basically, this device consists of an entrance window "A" having a photocathode 60 which is very sensitive to the wavelength-specific near-infrared light pulses to be utilized. A few hundred microns from the photocathode is the input face of a microchannel plate electron multiplier (MCP) labeled "B." The electrons which emerge from the MCP are accelerated by appropriate bias voltages to impact a phosphor screen 62 deposited on the inside of an output window Such image intensifiers can be used as fast electronic imaging shutters by biasing the photocathode 60 by an appropriate positive electrical potential relative to the front of the MCP, and then applying a short negative pulse to momentarily turn the device "on." As used in accordance with both the previous patent and the present invention, the shuttered detectors 22, 24 also include a photodiode coupled to the image-intensifier outer window "C" so that an electrical signal is obtained that corresponds to the image intensity appearing on output window "C". As indicated previously, both of the shuttered detectors 22 and 24 (also designated "S1" and "S2," "S3") of the previous patent would, of course, each include its own image intensifier for independent switching.

The speed with which an image intensifier can be turned on and off is limited by a phenomenon called "irising," in which the peripheral image field appears first while the center of the field is still dark (off). The reason for this is that the photocathode material has a relatively high resistance per unit area and a distributed capacitance, principally to the front of the MCP, and an electrode ring 64 is used in such devices to apply the gating voltage. When a fast negative pulse is applied to the electrode ring 64, it takes a finite if short time to charge the photocathode center relative to its periphery. Typically, this delay will be on the order of at least several nanoseconds, before the intensifier is fully turned on. The effects of such irising are negated as used in accordance in the present invention, since the image intensifier is only being used for shuttered light detection rather than imagery. Thus, by limiting the fiber optics applying the input photons to only the edge of the photocathode, adjacent the ring electrode 64, the delay in fully turning on the center of the photocathode is made entirely irrelevant.

In accordance with the present invention, both the system (apparatus) and processing of the time-related detected photon signals are simplified and substantially improved. This is based on apprehension of the fact that a number of important sources of error may be cancelled by taking the ratio of the number or representative value of at least two bursts of mutually time-spaced returning photons, i.e., those leaving the head of the patient and being coupled to the photon detection apparatus 20 on fiber optical cable 44, which are to be shutter-detected at points in time corresponding to two or more specifically designated time delays after introduction of the related wavelength-specific photons from source 10.

More particularly, the number of photons (N) received after a first time delay (t) may be expressed as:

$$N \propto TS \, e^{-\rho\sigma(\lambda,f)ct} \qquad \text{Eq. 1}$$

where:
T=transmission at the fiberoptic-skin interface
S=sensitivity of the shuttered-detector
ρ=density of hemoglobin molecules (α) to blood density
σ=cross-section of a hemoglobin molecule at wavelength A and fractional oxygen f
c=velocity of photons in tissue
t=time delay from injection If, in the expression set forth above, ρ is in units of molecules per cubic centimeter and σ is in units of square centimeters, then ρσ is the familiar linear absorption coefficient "μ" in units of inverse centimeters. Likewise, if c is units of centimeters per second and t is units of seconds, then ct is the pathlength in units of centimeters.

Using the basic expression set forth above as Equation 1, the number of photons received at a second time delay t is expressed as follows:

$$N' \propto T'S' \, e^{-\rho\sigma(\lambda,f)ct'} \qquad \text{Eq. 2}$$

By dividing Equation 2 by Equation 1, we get the following ratio:[1]

[1] Note that the differential pathlength, ΔP=c(t'−t), is known exactly.

$$\frac{N'}{N} = \left(\frac{T'}{T}\right)\left(\frac{S'}{S}\right) e^{-\rho\sigma(\lambda,f)c(t'-t)} \qquad \text{Eq. 3}$$

As can be seen from Equation 3 above, variations in the coupling of the fiber optics with the skin are cancelled, since with these very short times T'=T. Referring back to FIG. 1 and the accompanying discussion, it will of course be understood that each of the shuttered detectors 22, 24 will have its own characteristic sensitivity S, S'; however, in accordance with the invention, it is observed that if these two quantities could be made equal, they would also cancel, making the solution of the equation that much simpler. This novel and useful concept is accomplished in accordance with the present invention, and accomplished in a most effect way; i.e., a single image detector is utilized to switch each of the time-delayed photon quantities exiting the head of the patient, that carry the oxygen-related hemoglobin absorption information which is desired.

Figure 4:
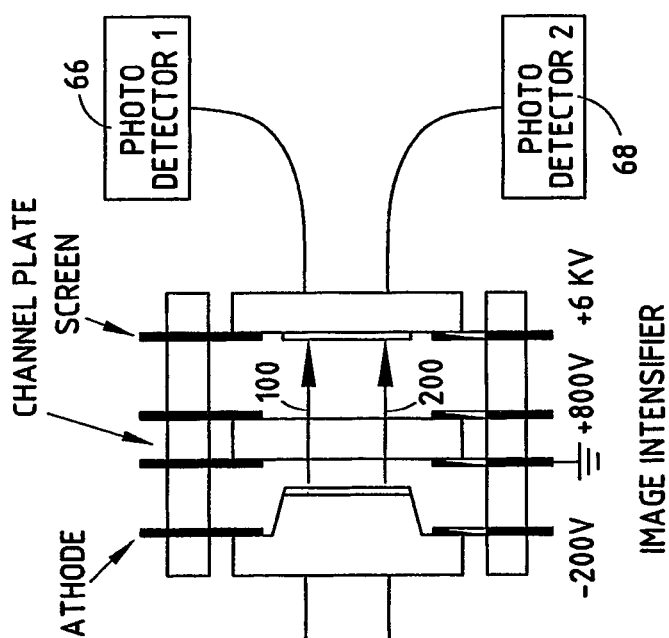
FIG. 4 is an enlarged, simplified drawing showing the image intensifier portion of the shutter detector, as utilized in accordance with the invention.

As indicated above, the shuttered detectors 22, 24 utilized in the preferred embodiment include a proximity-focused image intensifier, the output light from which is measured by a photodetector (as referred to above, and as described in detail in the prior patent identified above which is incorporated herein by reference). As disclosed in the prior patent, the termination of the fiber optic cable, (i.e. cable 44, as seen in FIG. 1) conducting the photons from the head is positioned at the edge of the image intensifier's photocathode to speed its response to the gating pulse by minimizing the distributed resistance and capacitance inherent in the thin photocathode, which causes the "irising" effect noted above. In accordance with the invention, a single image intensifier is utilized to provide two correlated but separate simultaneously acting shutters, by bringing a second fiberoptic cable (designated 144 in FIGS. 3 and 4) from the head of the patient to the same image intensifier, but positioning its termination at the side of the photocathode opposite that where cable 44 is terminated (i.e., 180° therefrom). By using this arrangement, all that is required to make the device operate as a pair of separate or detectors is the presence of a second photodetector (66, 68) on the image intensifier's output side (FIG. 4). These two photodetectors must be arranged to separately view the images appearing on the ends of the two input fiber optic cables 44, 144, as they appear separately mapped on the image intensifier output screen 62. In this regard, it should be pointed out that by utilizing this inventive concept, the same image intensifier may be utilized to provide even more than two such shutters, or optical switches.[2]

[2] The only limitation is the angular spatial resolution of the image intensifier around the edge of the photocathode and the corresponding map on the output screen. An inexpensive "streak camera" device could be built using a large number of input fibers each with small, uniformly stepped delays.

Figure 3:
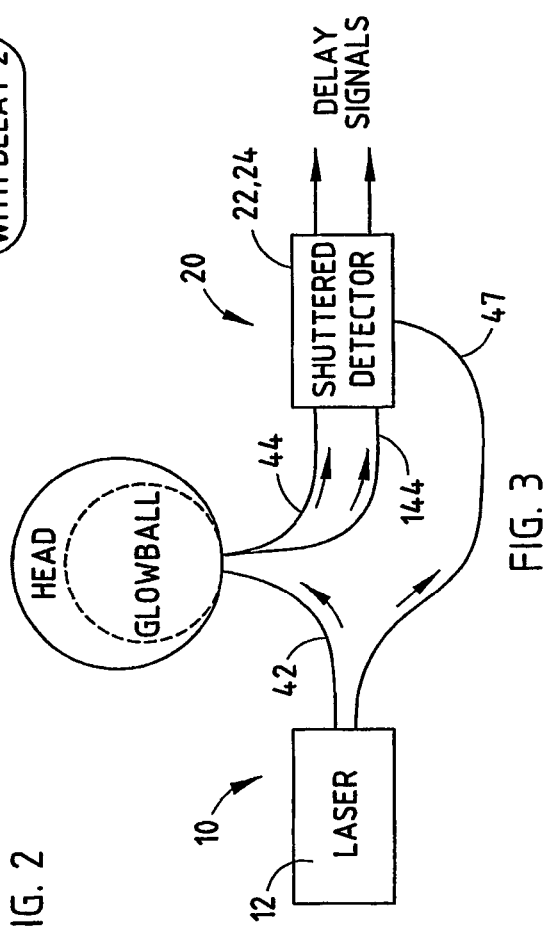
FIG. 3 is a simplified system block diagram illustrating a detection system in accordance with the present invention.

FIG. 3 provides a schematic representation of such an improved, simplified system, and the image intensifier portion thereof, comparable to that shown in FIG. 4 of the referenced prior patent and FIG. 2 herein, is shown in FIG. 4 herein. As will be seen from FIG. 3 herein, the photon detection fiberoptic 44, 144 extending from the head of the patient to the shuttered detector 22, 24 may advantageously be implemented by use of a single bifurcated or branched fiberoptic cable, one branch forming cable 44 and the other forming cable 144. Also, as schematically illustrated in FIG. 4 herein, and as noted above, photon input cable 44 is directly aligned with an output location of the image intensifier that is coupled to its own photodetector, designated 66 herein, and photon delivery cable 144 is directly aligned with an image-intensifier output coupled to its own photodetector, designated here 68. Accordingly, the burst of photons to be detected at a first time interval following the instant of photon injection, t, is indicated by the arrow 100, and the other such burst, at time t' following injection, is indicated by the other such arrow, designated 200. As shown in this example, where two separate branches carrying differently timed photon bursts (or images) are being switched by a single image intensifier, the input and output cables or other such optical connectors are preferably disposed 180° from each other around the edge of the photocathode. Of course, if a greater number of photon bursts was being detected, a corresponding greater number of separate cable branches would be used and each would be correspondingly equally spaced from the others around the edge of the photocathode.

With further reference to the system of the aforementioned prior patent, and as noted above, the two (or more) shuttered detectors 22, 24 are gated by a small portion of the input photon burst from source 10 (laser 12), by using two different fiberoptic cables (there designated 46 and 48) having two different lengths, so that the shuttered detectors are gated on at different points in time, thereby sampling or detecting the photons leaving the head at two different points in time, in effect taking "snapshots" at those points in time. In accordance with the present invention, the single shuttered detector 22, 24 is gated at a single point in time, utilizing a portion of the photons from the source directed toward the head. Although the single shuttered detector 22, 24 thus operates at a single and brief point in time, the different photon quantities which it detects at that single point in time actually emanate from the head of the patient at two closely spaced but different points in time, due to the precisely cut input cables 44 and 144. Thus, the outputs from the shuttered detectors which are applied to photodetectors 66 and 68 are specifically different, and comparatively unique, notwithstanding the fact that the shuttered detector is operated only a single time to switch photon inputs that occurred at different points in time.

As an example of such a system, assume that the source (laser) 12 produces the photon pulse at t=0 and the fiber optic conducting the light to the head (42) is 10 ns long. Assume the fiberoptic receiving the photons 44, 144 from the head is split into two cables (bifurcated) going to opposite points on the edge of the image intensifier photocathode, as described above, but with one of the branches cut to be 6 ns and the other branch 7 ns long. If the gating fiber (47) between the laser 12 and the shuttered detector 22, 24 is 21 ns long and cable branch 44 is 6 ns long while branch 144 is 7 ns long, the photons arriving over the 6 ns fiber (44) will have left the head 5 ns after injection while the photons arriving over the 7 ns fiber (144) will have left the head 4 ns after injection. Accordingly, with this system, the ratio of the two signals from the corresponding photodetectors 66, 68 will be independent of both time and amplitude ("jitter") in the shuttered detector gate, since S'=S.

Further improvements or enhancements in the system described in the previous patent are as follows. The first such feature, also comprising a part of the present invention, relates to the characteristics of the input and output fiberoptic cables, herein designated 42 and 44, 144 respectively. While it is obvious that the core material of these fibers should not scatter light, some such scattering is unavoidable. The very large injection pulse from the laser (12) initiates "reverberation" from scattering and reflection at the fiber ends that may persist long enough to interfere with the measurement of delayed light. Unlike the causes of this problem, its solution is not obvious; however, one measure which will or may help is to have the core material be deliberately partially absorbing. While the signal light passes through the fibers once, the reverberating light takes a longer path and will be discriminated against by such absorption.

The other item or feature has to do with insuring that the pulses used to gate the single shuttered (22, 24) detector on are of uniform amplitude. As indicated above, the photocathode of the image intensifier is biased off prior to the time of arrival of the laser-generated injection pulse (by a large positive voltage, which keeps the photoelectrons from getting to the microchannel plate), and it is only turned on (made negative) several nanoseconds later to measure the very small amount of delayed light from the head of the patient or test subject. However, the photocathode tends to "remember" the large initial pulse and release some electrons to the microchannel plate when turned on, even if there is no delayed light. This phenomenon was referred to as "persistence" in the prior patent referred to above.

Two operating parameters appear to be most important in eliminating this 'persistence'. Firstly, the larger the "off" bias, the better. In the particular implementation described and illustrated, increasing the "off" bias from +170 to +190 volts appears to reduce the persistence by two orders of magnitude. Secondly, it is important to control the amplitude of the larger negative gate "on" pulse so that it does not take the photocathode more than 20 v negative. Therefore, for a +190 volt "off" bias in this implementation, the gate "on" pulse peak amplitude should be very close to −210 v. Since the gate pulse is derived directly from a photodiode which is driven by a fraction (delayed) of the laser pulse, its reproducibility depends on the laser pulse amplitude stability. Since the laser's stability is much less than the 2% needed to hold the on voltage to 20%, it is believed advantageous to use avalanche transistors to completely isolate the laser-generated photodiode gate pulse from the image intensifier photocathode. The photodiode will trigger an avalanche breakdown in a string of transistors that will then generate their own gate pulses with amplitudes that are independent of the laser output stability. Based on measurements taken of representative circuits, the avalanche transistor breakdown occurs in less than ins. (For a reference with respect to avalanche transistors, see Jinyuan L. Bing S. Zenghu C; "*High voltage fast ramp pulse generation using avalanche transistor,*" Rev. Sci. Inst 69, 3066–67, 1998).

Figure 5:
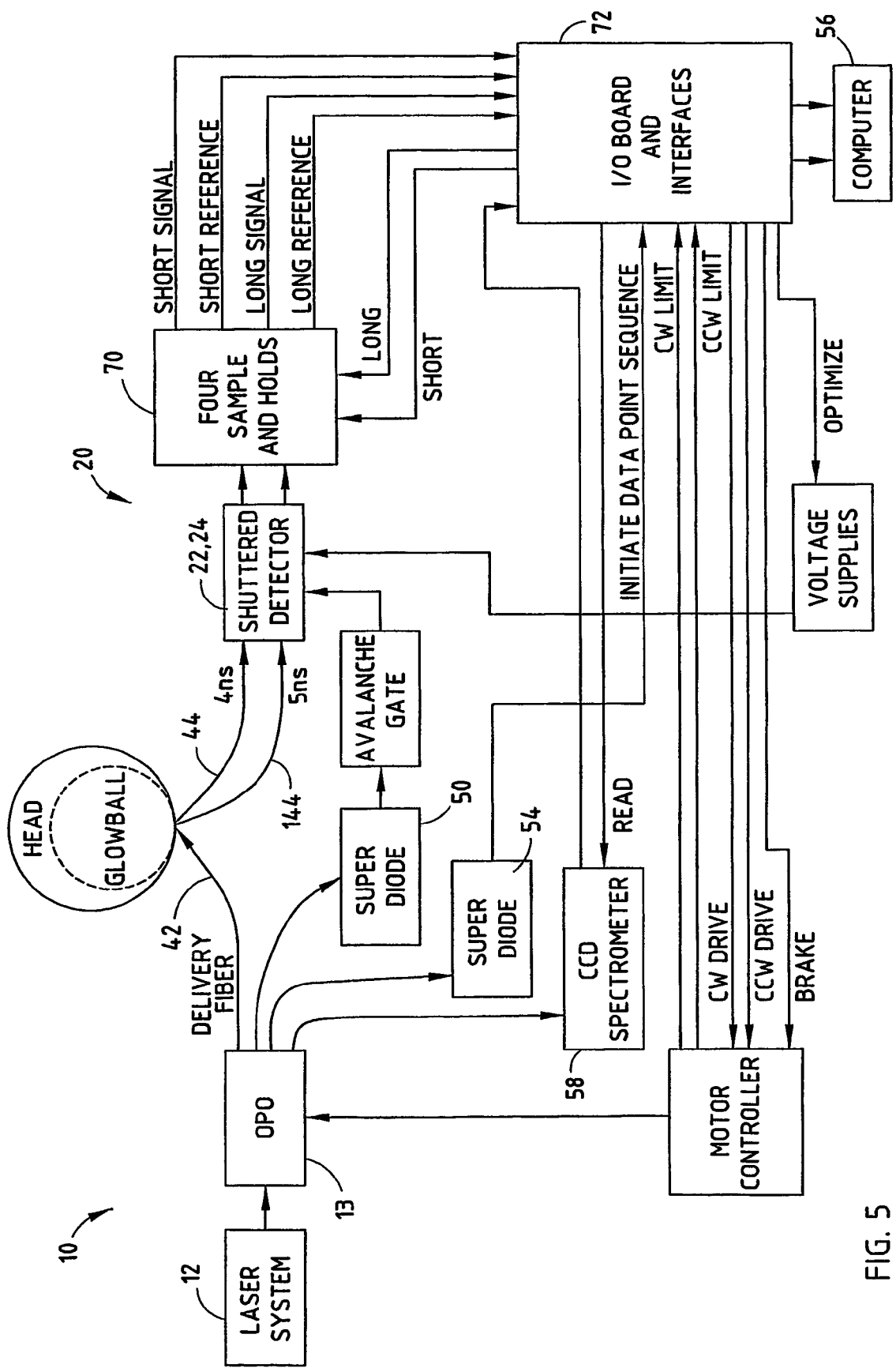
FIG. 5 is a schematic block diagram showing a preferred and more detailed embodiment of the present invention.

FIG. 5 is a schematic block diagram showing a preferred and more particular embodiment of the overall system of the invention shown in FIG. 3. The laser system 12 for the preferred embodiment shown in FIG. 5 consists of a flashlamp-excited Nd:YAG laser with its 5 ns output pulses of infrared light (1064 nm) closely coupled to a second harmonic generator ("SHG"), which converts the wavelength to green light (532 nm) and width to 4 ns.[3] The pulse of light from the SHG is then closely coupled to an optical parametric oscillator (OPO) 13 where the wavelength is tuned to the range of 700 to 950 nm depending on the angle of its internal prism with pulse widths of 3 ns. The pulse of infrared photons from the OPO 13 (or laser) is divided into four parts[4]. Most such photons go to the head via the delivery fiber 42. Another part of them goes to a super diode 50 which triggers the avalanche gate 52, turning on the shuttered detector 22, 24. The third photon pickoff goes to another super diode 54, which signals the computer 56 to start a new data point sequence. A fourth photon part goes to the CCD spectrometer 58, which measures the wavelength of the photons in the pulse.

[3] Another useful source is a Quantel Nd:YAG laser
[4] Actually, more laser pulse pickoffs may also be used—notably to drive a Pockels Cell used to quench the tail of the pulse.

With further reference to FIG. 5, light emerging from the head is carried to the shuttered detector inputs by two fibers 44, 144 that differ in length by ins. The two electrical equivalent outputs from the shuttered detector 22, 24 are sampled and digitized, and coupled to the computer 56 by appropriate components 70, 72, as labeled, under the control of the console computer and associated software.

Figure 6:
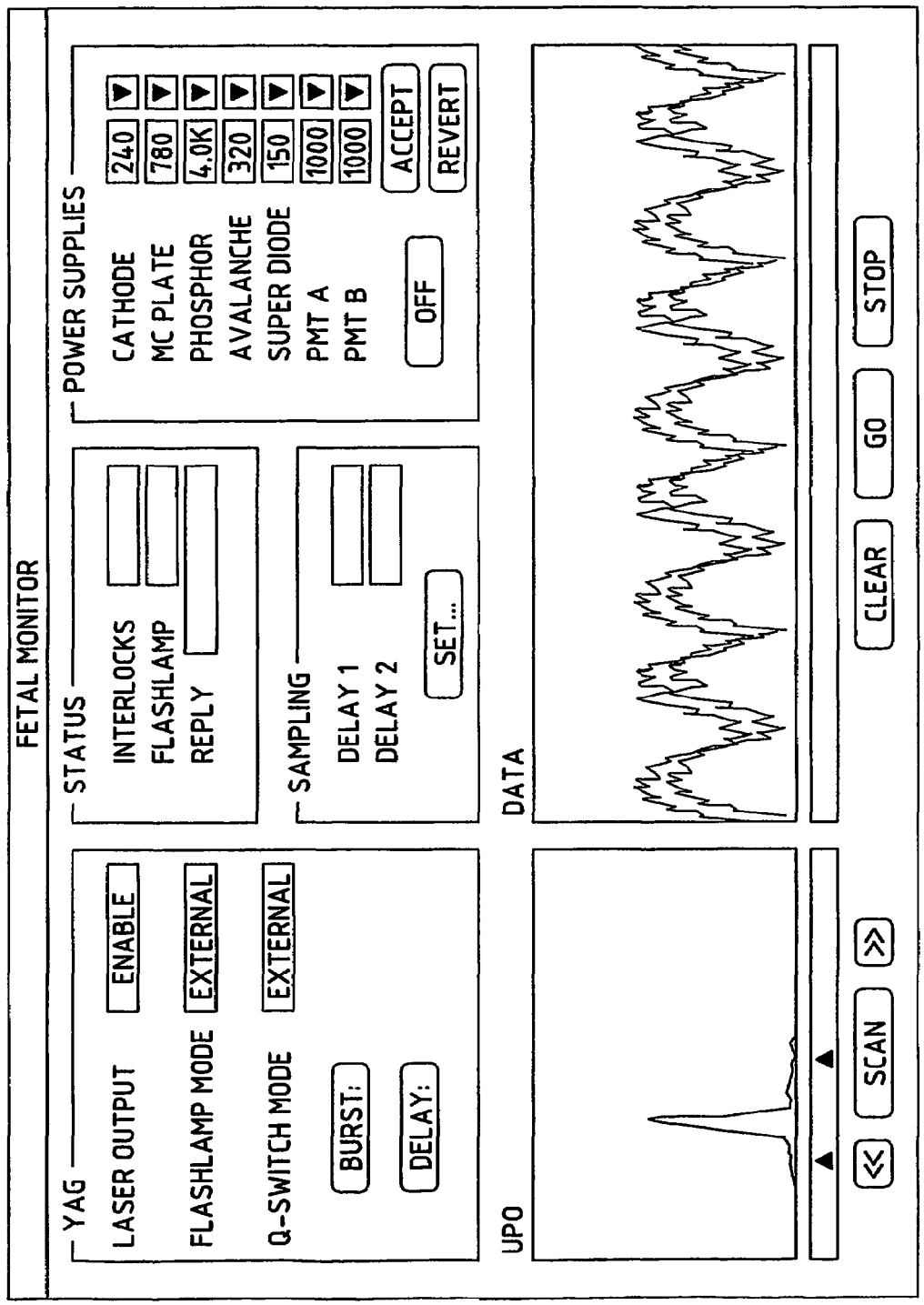
FIG. 6 is a pictorial view showing an exemplary visual display for use in operating the system.

FIG. 6 is a pictorial view showing an exemplary display-type user interface for use in operating a system in accordance with the invention. The system gathers data in a "list" mode. That is, for each laser (12) pulse the computer (56) saves the time, the signal and reference data for the two PMT's, the amplitude and wavelength of the pulse from the OPO, and several bits of "housekeeping" data. This data is binned (made into a histogram) on the fly to build up an absorption spectrum of the chromophores within the glow-ball and displayed on the computer monitor.

In the operator interface display shown in pictorial view FIG. 6, the box at top left ("VR6") sets the laser operating parameters. The middle box ("Status") displays the system status, and the box at the right ("Power Supplies") allows the operator to set the power supply voltages. The dynamic display on the lower left ("OPO") continuously shows the wavelength of each pulse and allows the wavelength range to be set. The display at lower right ("Data") continuously scrolls the outputs of the two channels.

As will now be readily apparent to those skilled in the art, a highly novel and advantageous improvement is provided herewith, both in connection with the particular fetal cerebral oximeter apparatus which forms the primary focus of this patent, and also, in a broader sense, in connection with the gating of such optical systems generally; i.e. the use of a single image intensifier that simultaneously sequentially gates a plurality of different optical circuits also has substantial potential advantage for various different applications. Consequently, both such aspects are to be considered part of this invention, as are the two other aspects set forth immediately above.

It is believed that those skilled in the art will readily recognize the novel and unobvious character of the inventions disclosed above, and also recognize the wide scope of applicability and high degree of advantage which they possess and provide. Of course, the above description is to be considered that of preferred embodiments only. Modifications and variations of this and other such embodiments may well occur to those skilled in the art and to those who make or use the invention after learning of it through access to such preferred embodiments. Accordingly, it is to be understood that the embodiment shown in the drawings and described above is merely for illustrative purposes and should not be used to limit the scope of the invention, which is to be interpreted according to the principles of patent law, including the doctrine of equivalents.

The invention claimed is:

1. Apparatus for spectrophotometrically monitoring hemoglobin oxygenation in a test subject, comprising in combination:
    a source of photons having a desired wavelength;
    a probe coupled to said source to optically access a single location on the test subject by injecting photons into said subject from said source at said location and for receiving photons exiting said subject at said location after injection;
    a photon-conducting device operatively associated with said probe to receive a stream of said exiting photons and to produce at least two differently timed streams of photons therefrom;
    a shuttered device coupled to said photon-conducting device to receive said at least two differently-timed photon streams and simultaneously switch each of said two streams on and off to create a pair of different photon bursts therefrom; and
    a detector coupled to said shutter device to receive said pair of separate photon bursts and provide corresponding output signals for processing.

2. The apparatus for monitoring hemoglobin oxygenation in a test subject according to claim 1, wherein said photon-conducting device operatively associated with said probe comprises at least two fiberoptics having different effective light-conducting lengths to create said at least two differently-timed photon streams.

3. The apparatus for monitoring hemoglobin oxygenation in a test subject according to claim 1, wherein said shutter device comprises an image intensifier.

4. The apparatus for monitoring hemoglobin oxygenation in a test subject according to claim 3, wherein said photon-conducting device operatively coupled to said probe comprises at least two fiberoptics having different effective light-conducting lengths to create said at least two differently-timed photon streams.

5. The apparatus for monitoring hemoglobin oxygenation in a test subject according to claim 4, wherein each of said at least two fiberoptics is coupled to said image intensifier to provide inputs which are switched simultaneously thereby.

6. The apparatus for monitoring hemoglobin oxygenation in a test subject according to claim 5, wherein said image intensifier includes a generally annular photocathode and each of said at least two fiberoptics is terminated at said photocathode in a position spaced from the other, whereby said image intensifier produces at least two outputs and each such output is separately representative of a different one of said inputs.

7. The apparatus for monitoring hemoglobin oxygenation in a test subject according to claim 6, wherein said image intensifier has an output element, and including at least two output conductors coupled to said output element to receive separate output signals therefrom, each of said separate output signals representative of a different one of said inputs.

8. The apparatus for monitoring hemoglobin oxygenation in a test subject according to claim 7, wherein each of said at least two output conductors is coupled to said image intensifier output element in direct alignment with a different one of said at least two image intensifier inputs.

9. The apparatus for monitoring hemoglobin oxygenation in a test subject according to claim 1, including a fiberoptic conductor coupled between said source of photons and said probe for providing said photons for injection into said subject, wherein said fiberoptic conductor comprises a partially absorbing fiberoptic to discriminate against photon stream reverberation due to scatter and reflection efforts.

10. The apparatus for monitoring hemoglobin oxygenation in a test subject according to claim 3, including a coupling between a gating electrode of said image-intensifier and said photon source, whereby said image intensifier is gated on and off by operation of said source, said coupling including a device to convert from said source into a corresponding electrical signal.

11. The apparatus for monitoring hemoglobin oxygenation in a test subject according to claim 10, wherein said coupling includes an avalanche transistor array.

12. A method of processing optically produced hemoglobin oxygenation data which includes at least two signals that are respectively representative of at least two quantities of examination light which are emitted from a test subject at different points in time with respect to each other following the input of related and corresponding examination light pulsed into said test subject, said method comprising the step of computing a value for each of said at least two signals, taking the ratio of said at least two signal values to thereby cancel out and thus remove error sources common to each of said at least two values, and at least one of displaying the ratio, and providing the ratio to a computer for further processing.

13. The method of claim 12, wherein said computational method includes use of the equation $$N \propto TS\, e^{-\rho \sigma(\lambda, f) ct}$$

where:
N=number of photons (or equivalent, e.g., value)
T=transmission at the fiberoptic-skin interface
S=sensitivity of the shuttered-detector
ρ=density of hemoglobin molecules (α) to blood density
σ=cross-section of a hemoglobin molecule at wavelength λ and fractional oxygen f
c=velocity of photons in tissue, and
t=time delay from injection.

14. The method of claim 13, wherein the value "S" in said computational method is made identical in the computation for each of said at least two signal values by using a common shuttered-detector for determining each of said at least two signal values, whereby said value "S" will cancel out when said ratio of signal values is taken.

15. The method of claim 13, wherein the value "T" in said computational method is made to be substantially identical in the computation for each of said at least two signal values by inputting said examination light corresponding to said at least two streams of emitted examination light at substantially the same point in time.

16. The method of claim 12, including the step of using a fast shuttered detector to determine said at least two quantities of examination light.

17. The method of claim 16, wherein said step of using a fast shuttered detector comprises using a single such detector to determine each of said at least two quantities of light.

18. The method of claim 16, wherein said step of using a fast shuttered detector is carried out by using an image-intensifier.

19. A method of monitoring hemoglobin oxygenation in a test subject, comprising the steps of:
   injecting a quantity of photons having a predetermined wavelength into said test subject at a predetermined time and location;
   optically accessing said predetermined location on said test subject to receive photons exiting said test subject at at least two different timed intervals following said time of injecting;
   converting said received photons exiting said test subject at at least two different timed intervals into at least two corresponding concurrent signals for subsequent evaluative processing; and
   least one of displaying the at least two corresponding concurrent signals, and providing the at least two corresponding concurrent signals to a computer for further processing.

20. The method of claim 19, wherein said step of converting said photons exiting said test subject at different times into corresponding concurrent signals is carried on simultaneously.

21. The method of claim 20, wherein said step of converting is carried out at least in part by applying said photons to a common switching device as separate photon groupings.

22. The method of claim 19, wherein said step of converting said photons into corresponding concurrent signals includes the step of delaying a photon grouping received at a longer time interval after injection into said test subject at a first time with respect to a different grouping injected at a second and subsequent time.

23. The method of claim 19, wherein said step of converting is carried out at least in part by applying said photons to a common switching device as separate photon groupings.

24. The method of claim 19, wherein said corresponding concurrent signals are assigned corresponding valuations and said evaluative processing includes taking a ratio of said corresponding signal valuations.

* * * * *

UNITED STATES PATENT AND TRADEMARK OFFICE
CERTIFICATE OF CORRECTION

PATENT NO. : 7,221,969 B2  Page 1 of 1
APPLICATION NO. : 10/506158
DATED : May 22, 2007
INVENTOR(S) : Stoddart et al.

It is certified that error appears in the above-identified patent and that said Letters Patent is hereby corrected as shown below:

Column 2, line 2;
   "ins)" should be --1ns)--.
Column 2, line 62;
   "ins)" should be --1ns)--.
Column 3, line 34;
   "ins" should be --1ns--.
Column 3, line 50;
   After "window" insert -- "C."--; Start new paragraph at "Such".
Column 7, line 25;
   "ins" should be --1ns--.
Column 7, line 54;
   "ins" should be --1ns--.
Column 9, claim 10, line 40;
   After "convert" insert --photons--.
Column 10, claim 19, line 39;
   Before "least" insert --at--.
Column 10, claim 24, line 60;
   "claim 19" should be --claim 20--.

Signed and Sealed this

Thirtieth Day of October, 2007

JON W. DUDAS
*Director of the United States Patent and Trademark Office*